(12) United States Patent
Cross

(10) Patent No.: US 11,590,301 B2
(45) Date of Patent: Feb. 28, 2023

(54) AEROSOL-GENERATING DEVICE COMPRISING A POWDER DE-AGGLOMERATING ACTUATOR

(71) Applicant: PHILIP MORRIS PRODUCTS S.A., Neuchatel (CH)

(72) Inventor: David Cross, Letchworth (GB)

(73) Assignee: Philip Morris Products S.A., Neuchatel (CH)

( * ) Notice: Subject to any disclaimer, the term of this patent is extended or adjusted under 35 U.S.C. 154(b) by 742 days.

(21) Appl. No.: 16/485,637

(22) PCT Filed: Feb. 27, 2018

(86) PCT No.: PCT/EP2018/054724
§ 371 (c)(1),
(2) Date: Aug. 13, 2019

(87) PCT Pub. No.: WO2018/158207
PCT Pub. Date: Sep. 7, 2018

(65) Prior Publication Data
US 2020/0046020 A1    Feb. 13, 2020

(30) Foreign Application Priority Data

Feb. 28, 2017   (EP) .................................... 17158344

(51) Int. Cl.
*A61M 15/06*    (2006.01)
*A61M 11/04*    (2006.01)
(Continued)

(52) U.S. Cl.
CPC ............. *A61M 15/06* (2013.01); *A24F 40/40* (2020.01); *A24F 42/20* (2020.01); *A24F 42/60* (2020.01);
(Continued)

(58) Field of Classification Search
CPC ............. A61M 15/06; A61M 15/0041; A61M 2016/0015; A61M 2202/064;
(Continued)

(56) References Cited

U.S. PATENT DOCUMENTS 3,948,264 A * 4/1976 Wilke ............... A61M 15/0028
128/203.15
5,461,695 A    10/1995 Knoch
(Continued)

FOREIGN PATENT DOCUMENTS

CN    105307526    2/2016
RU    2012152885   6/2014
(Continued)

OTHER PUBLICATIONS

PCT Search Report and Written Opinion for PCT/EP2018/054724 dated May 16, 2018 (14 pages).
(Continued)

*Primary Examiner* — Elliot S Ruddie
(74) *Attorney, Agent, or Firm* — Mueting Raasch Group

(57) ABSTRACT

The present invention relates to an aerosol-generating device (1) for generating an aerosol by dispersing an aerosol-forming powder (31) into an airflow. The device comprises a device housing (2) which comprises an airflow passage therethrough and which is configured to receive a capsule (30) that contains the aerosol-forming powder to be discharged into the airflow passage. The device further comprises a magnetic actuator (40) which is configured to generate a movement of the capsule when being received in the device housing for de-agglomerating the aerosol-forming powder within the capsule. The invention further relates to an aerosol-generating system comprising an aerosol-
(Continued)

generating device according to the invention and an aerosol-forming powder containing capsule for use with the aerosol-generating device.

13 Claims, 3 Drawing Sheets

(51) Int. Cl.

| | |
|---|---|
| *A24F 40/40* | (2020.01) |
| *A24F 42/20* | (2020.01) |
| *A24F 42/60* | (2020.01) |
| *A61M 15/00* | (2006.01) |
| *A61M 16/00* | (2006.01) |
| *A24F 40/20* | (2020.01) |

(52) U.S. Cl.
CPC ............ *A61M 11/042* (2014.02); *A24F 40/20* (2020.01); *A61M 15/0041* (2014.02); *A61M 2016/0015* (2013.01); *A61M 2202/064* (2013.01); *A61M 2205/0272* (2013.01)

(58) Field of Classification Search
CPC .. A61M 2205/0272; A61M 2205/3375; A61M 2205/8206; A61M 15/0005; A61M 15/003; A61M 15/0036; A61M 2205/14; A61M 11/041; A61M 11/042; A24F 40/20; A24F 40/40–42; A24F 40/46–465; A24F 42/20; A24F 42/60; H01F 7/1607
USPC .......................................................... 138/109
See application file for complete search history.

(56) References Cited

U.S. PATENT DOCUMENTS

| | | | | |
|---|---|---|---|---|
| 5,694,920 | A | 12/1997 | Abrams et al. | |
| 6,328,033 | B1 * | 12/2001 | Avrahami ........... | A61M 15/001 128/203.19 |
| 9,078,985 | B2 | 7/2015 | Maynard et al. | |
| 2011/0220234 | A1 | 9/2011 | Haas | |
| 2013/0000640 | A1 * | 1/2013 | Maynard ........... | A61M 15/0035 128/203.15 |
| 2017/0055583 | A1 * | 3/2017 | Blandino ................ | H05B 6/06 |

FOREIGN PATENT DOCUMENTS

| | | |
|---|---|---|
| WO | 20110009925 | 1/2011 |
| WO | WO 2012/026963 | 3/2012 |
| WO | 20150177253 | 11/2015 |
| WO | WO 2015/166344 | 11/2015 |
| WO | WO 2017/109678 | 6/2017 |
| WO | WO 2018/007887 | 1/2018 |
| WO | WO 2018/100461 | 6/2018 |
| WO | WO 2018/100462 | 6/2018 |

OTHER PUBLICATIONS

Chinese Office Action for CN Application No. 201880014134.5 issued by the Chinese Patent Office dated Nov. 17, 2021:12 pgs. including English translation.
Office Action issued in Russia for Application No. 201913 0496 dated Jul. 5, 2021 (8 pages). English translation included.

* cited by examiner

AEROSOL-GENERATING DEVICE COMPRISING A POWDER DE-AGGLOMERATING ACTUATOR

This application is a U.S. National Stage Application of International Application No. PCT/EP2018/054724 filed Feb. 27, 2018, which was published in English on Sep. 7, 2018, as International Publication No. WO 2018/185207 A1. International Application No. PCT/EP2018/054724 claims priority to European Application No. 17158344.6 filed Feb. 28, 2017.

The present invention relates to an aerosol-generating device for generating an aerosol from an aerosol-forming powder. The invention further relates to an aerosol-generating system which comprises such an aerosol-generating device and an aerosol-forming powder containing capsule for use with the aerosol-generating device.

Aerosol-generating devices based on dispersing an aerosol-forming powder into an airflow are generally known from prior art. For example, such devices may be used to treat respiratory diseases by delivering a dry powder comprising a pharmaceutical in aerosol form to a patient's respiratory tract. Likewise, such devices may be used for delivering a nicotine and/or flavored powder to a user in order to provide a user experience. In particular, such devices are known as powder inhalation devices or powder inhalers. The devices may be configured to receive a capsule which contains the aerosol-forming powder to be dispersed. Yet, the powder within the capsule may tend to agglomerate which may be disadvantageous with regard to aerosol formation.

Therefore, it would be desirable to have an aerosol-generating device and system for generating an aerosol from an aerosol-forming powder offering the advantages of prior art solutions without their limitations. In particular, it would be desirable to have an aerosol-generating device and system having means for de-agglomerating the aerosol-forming powder within the capsule.

According to the invention there is provided an aerosol-generating device for generating an aerosol by dispersing an aerosol-forming powder into an airflow. The device comprises a device housing having an airflow passage therethrough. The device housing is configured to receive a capsule that contains the aerosol-forming powder to be discharged into the airflow passage. The aerosol-generating device further comprises a magnetic actuator which is configured to generate a movement of the capsule when being received in the device housing for de-agglomerating the aerosol-forming powder within the capsule.

According to the invention it has been recognized that powder de-agglomeration may be easily achieved by applying a movement to the capsule such as to loosen the powder within the capsule. Advantageously, this kind of powder de-agglomeration only relies on a mechanical de-agglomeration of the aerosol-forming powder without the need of any de-agglomerating additives in the powder. Furthermore, the de-agglomerating movement advantageously causes the powder to be swirled up which facilitates the discharge of the powder into the airflow passage and, thus, intensifies the aerosol formation.

Preferably, the movement to be generated and induced onto the capsule is a shaking movement or a vibrational movement or a pulsating movement. The movement may be or reciprocating or oscillatory movement. Preferably, the shaking movement, vibrational movement or pulsating movement may comprise a frequency in the range of 20 Hz to 20 kHz, in particular 20 Hz to 1 kHz, preferably 50 Hz to 500 Hz, most preferably 100 Hz to 500 Hz. In particular, the shaking movement, vibrational movement or pulsating movement may comprise a resonance frequency of the powder containing capsule. Advantageously, this allows for agitating the powder within the capsule as efficiently as possible.

The movement may be a linear movement or a rotational movement or a combination thereof. Accordingly, the magnetic actuator may be a linear magnetic actuator or a rotary magnetic actuator.

As used herein, the term 'magnetic actuator' refers to any actuator using magnetic effects, in particular a magnetic field, to generate forces which impact on the motion of a part of the actuator or an object coupled to the actuator. In particular, the magnetic actuator may be based on magnetic forces acting at distance, such as, the reluctance force and Lorentz force.

The magnetic actuator may comprise a stationary part and a movable part. As used herein, the movable part is movable relative to the stationary part, whereas the stationary part is stationary with regard to the aerosol-generating device. The movable part may be configured to move in response to a magnetic field or magnetic fields generated within the actuator which causes a magnetic force between the stationary part and the movable part. As used herein, the movable part of the magnetic actuator is also referred to as 'armature' as will be explained in more detail below.

For generating a movement of the capsule accordingly to the invention, the movable part may be connectable to the capsule in order to transfer its magnetically induced movement relative to the stationary part onto the capsule.

As will be also further explained in more details below, the capsule itself may constitute the movable part of the actuator that is directly actuated by a stationary part of the actuator. The capsule may be either part of the actuator or may be a stand-only object separate from the actuator, which is not a part of the actuator. In particular, the actuator may only comprise a stationary part generating a magnetic force which directly impacts on the capsule, that is, on the motion of the capsule. In this case, the capsule may comprise means, for example magnetic or electrically conductive materials, for direct coupling with the magnetic field such as to produce a force that vibrates the capsule.

The magnetic field or the magnetic fields—which the actuating force of the magnetic actuator relies on—may be generated by either one of the stationary part, the movable part or the both, the stationary part and the movable part.

The magnetic field or the magnetic fields may be generated by an electrical current running through a wire, such as through one or more windings of a magnetic coil. Therefore, the magnetic actuator according to the present invention may be an electrically driven magnetic actuator.

In particular, the magnetic actuator according to the present invention may comprise at least one magnetic coil for generating a magnetic field. Magnetic coils advantageously provide a high degree of controllability of the magnetic field. In particular, magnetic coils allow for varying the strength of the magnetic field by just varying the current running therethrough. Moreover, magnetic coils may be easily designed to provide any desired field geometry in accordance with specific requirements of the magnetic actuator. As used herein, the terms 'magnetic coil' and 'magnetic field' generically also comprise the terms 'electromagnetic coil' and 'electromagnetic field'. Accordingly, the terms 'magnetic force' and 'magnetic effect' comprise the terms 'electromagnetic force' and 'electromagnetic effect'.

The magnetic actuator according to the present invention may also comprise at least one permanent magnet to generate a magnetic field that induces a motive force between the stationary part and the movable part of the magnetic actuator. Preferably, the at least one permanent magnet comprises a rare-earth magnet made from alloys of rare-earth elements, such as a samarium-cobalt magnet or a neodymium magnet. Rare-earth magnets advantageously are the strongest type of permanent magnets made, producing significantly stronger magnetic fields than other types such as ferrite or alnico magnets. Of course, the at least one permanent magnet may also comprise ferrite or alnico magnet.

The at least one magnetic coil may be either stationary or movable with regard to the aerosol-generating device, in particular with regard to a main body of the aerosol-generating device. Accordingly, the magnetic coil may be either part of a movable part or a stationary part of the actuator. Vice versa, either a stationary part or a movable part of the actuator may comprise at least one magnetic coil. Of course, also both, the stationary and the movable part of the actuator, may each comprise at least one magnetic coil, that is, at least one stationary magnetic coil and at least one movable magnetic coil, respectively.

Likewise, the at least one permanent magnet may be either stationary or movable with regard to the aerosol-generating device. Accordingly, the permanent magnet may be either part of a movable part or a stationary part of the actuator. Vice versa, either a stationary part or a movable part of the actuator may comprise at least one permanent magnet.

In general, the magnetic actuator may be a moving coil actuator or a moving magnet actuator. In a moving coil actuator, a movable magnetic coil is placed in static magnetic field, such as in static magnetic field of a stationary permanent magnet or another magnetic coil being stationary relative to the movable magnetic coil. When driven by a current, the movable magnetic coil is submitted to the Lorentz force causing a movement of the coil. This force is proportional to the applied current. Advantageously, this allows for accurately controlling the force and thus the movement of the movable magnetic coil. Moving coil actuators are generally also known as voice coil actuators. Vice versa, in a moving magnet actuator, a movable permanent magnet is placed in a stationary magnetic field, such as in a stationary magnetic field generated by a stationary magnetic coil or coil arrangement. By reversing the polarity of the stationary field, the movable permanent magnet may be actuated, for example in a rotational or linear movement. Advantageously, moving magnet actuators may provide high actuating forces.

Preferably, the magnetic actuator according to the present invention comprises at least one stationary magnetic coil within the device housing for generating a magnetic field. Having the magnetic coil stationary within the device housing advantageously reduces the complexity of the aerosol-generating device, thus allowing for a simple design that is robust and inexpensive to manufacture. In particular, a stationary magnetic coil does not require any means for transferring electrical power into the moving system of the actuator.

The magnetic coil may be a flat spiral magnetic coil or a helical magnetic coil. Helical coils advantageously allow for generating homogenous fields. Flat spiral coils advantageously allow for designing a compact device. The term 'flat spiral coil' as used herein covers coils that are planar as well as flat spiral coils that are shaped to conform to a curved surface. The flat spiral coil may have a circular shape or may have a generally oblong or rectangular shape. The magnetic coil can be held within the device housing. In particular, the magnetic coil may be positioned on or adjacent an inner surface of the device housing, that is within a wall of the material of the device housing. The magnetic coil may be arranged in a main body or in a mouthpiece of the device.

As counterpart to the stationary part of the magnetic actuator, in particular to the at least one stationary magnetic coil mentioned before, the magnetic actuator according to the present invention may further comprise a movable armature. As used herein, the term 'movable armature' generally refers to any movable element, component or part of the magnetic actuator that is configured to move in response to a magnetic field that is generatable by a stationary part of the magnetic actuator, in particular by a stationary magnetic coil. Thus, in operation of the actuator, an electromotive force is created between the armature and the magnetic field of the stationary part which causes the armature to move. Contrary to some definitions of the term 'armature' as occasionally used in electrical engineering, the armature—as referred to herein—does not need to or even does not carry any electrical current. Instead, the armature—as referred to herein—preferably comprises at least one magnetic material to interact with the magnetic field of the stationary part of the actuator.

As used herein, the term 'magnetic material' refers to a magnetizable or permanently magnetized material. The magnetic material may be either magnetically soft, such as a soft iron material, or magnetically hard, such as a permanent magnet. The magnetic material may be a ferromagnetic material or a ferrimagnetic material. For example, the magnetic material may comprise iron, ferromagnetic steel or a permanent magnet, such as a samarium-cobalt magnet or a neodymium magnet.

For generating the powder de-agglomerating movement of the capsule according to the invention, the movable armature is connectable, in particular fixedly and/or permanently connectable to the capsule such as to transfer its movement onto the capsule. In general, the armature may be connectable to the capsule by any suitable means. In particular, the armature may be connectable to the capsule by form-fitting, frictional-fitting, clamping, piercing or magnetic means. The armature may be connectable to the capsule via a holder that is configured to receive and hold the capsule within the device housing. The holder may be a form-fitting, frictional-fitting, clamping, piercing or magnetic holder. In particular, the holder may be part of the armature. Likewise, the armature may comprise or form a holder to receive and hold the capsule within the device housing. The armature may be connectable to the capsule via a linear or rotational shaft of the magnetic actuator.

According to one configuration, the magnetic actuator of the present invention may be a rotary magnetic actuator. In particular, the magnetic actuator may be an electromotor, preferably a permanent magnet motor. A permanent magnet motor is a type of brushless electric motor that uses permanent magnets rather than windings in the moving part.

Accordingly, the magnetic actuator may comprise at least one stationary magnetic coil and a rotatable armature. The rotatable armature comprises a least one rotatably mounted permanent magnet that is configured to rotate in response to a magnetic field of the magnetic coil such as to cause a rotational movement of the capsule when being connected to the armature. In this configuration, the magnetic actuator is a rotating magnet actuator. In particular, the stationary magnetic coil may be part of or constitute a stator, whereas the rotatably mounted permanent magnet may be part of or constitute a rotor.

By having permanent magnets rather than windings in the moving part of the actuator, the actuator does not need any commutator or slip ring or brushes. Thus, a rotating magnet actuator proves advantageous with regard a simple design that is robust and inexpensive to manufacture.

Of course, the rotary magnetic actuator described as before may also comprise a plurality of stationary magnetic coils, in particular a stationary magnetic coil arrangement. Likewise, the rotary magnetic actuator, that is the movable armature or the rotor, may comprise a plurality of rotatably mounted permanent magnets, in particular a rotatably mounted permanent magnet arrangement comprising a plurality of permanent magnets.

The stationary magnetic coil or coil arrangement may be configured to generate an alternating magnetic field causing the at least one permanent magnet or the permanent magnet arrangement to rotate. In particular, the alternating magnetic field may be a rotating magnetic field. In order to intensify the de-agglomeration of the powder within the capsule, the stationary magnetic coil or coil arrangement may be operated in a pulsed mode such as to generate a magnetic field that is alternatingly switched on and off and thus causes a pulsed rotational movement of the armature and the capsule connected thereto. Alternatively, the actuator coil may be operated such as to generate a slow continuous rotation movement of the armature and the capsule connected thereto. The slow continuous rotation movement may comprise a rotational speed equal to or less than 200 rounds per minute, in particular equal to or less than 100 rounds per minute, preferably equal to or less than 60 rounds per minute.

The stationary magnetic coil, that is the windings of the stationary coil, may be wound on a pole shoe to form magnetic poles when energized with current. For example, the pole shoe may be a laminated soft iron magnetic core. The magnetic poles are arranged such that the permanent magnet or the permanent magnet arrangement may rotate in between.

The direction of magnetization of the at least one permanent magnet preferably is perpendicular to the axis of rotation. The armature or the rotors may be radially magnetized, that is, having north and south poles alternating along the circumference of the rotor.

Preferably, the at least one permanent magnet comprises a rare-earth magnet made from alloys of rare-earth elements, such as a samarium-cobalt magnet or a neodymium magnet.

The at least one permanent magnet may be mounted on a rotational shaft for supporting its rotational movement. The rotational shaft itself may be rotatably mounted within the device housing. For this, the aerosol-generating device, in particular the magnetic actuator may comprise at least one, preferably two bearings, such as journal bearings, for supporting the rotational shaft. The rotational shaft may be also used for connecting the capsule to the actuator. In particular, the rotational shaft may be attached to or may be part of a piercing tube that is configured to pierce the capsule, in particular to piercingly couple with the capsule. The piercing tube may be also configured to fluidly connect the interior of the capsule with the airflow passage through the device housing. Accordingly, the rotational shaft may be hollow. For example, the rotational shaft may be a tube that is fluidly connected to or part of the airflow passage through the device housing.

According to another configuration, the magnetic actuator of the present invention may be configured to generate a linear movement of the capsule. In particular, the magnetic actuator may be a linear magnetic actuator, for such as a linear electromotor.

Accordingly, the magnetic actuator may comprise at least one stationary magnetic coil and a linearly movable armature. The linearly movable armature may comprise a slidably mounted permanent magnet configured to linearly move in response to a magnetic field of the magnetic coil such as to cause a linear movement of the capsule when being connected to the armature. In this configuration, the linear magnetic actuator is a linear moving magnet actuator.

The direction of magnetization of the at least one permanent magnet preferably is parallel to the axis of its linear movement.

The at least one stationary magnetic coil may be configured to generate an axial magnetic field along a linear axis of movement of the slidably mounted permanent. Depending on the orientation of the current powering the stationary magnetic coil, the slidably mounted permanent magnet is either repelled or attracted by the magnetic field of the stationary magnetic coil. Thus, by applying an alternating current to the stationary magnetic coil an alternating magnetic field may be generated to cause a reciprocating linear movement of the permanent magnet and the capsule attached thereto.

Alternatively, the linear magnetic actuator may comprise two stationary magnetic coils arranged at a distance along the linear axis of movement of the slidably mounted permanent magnet. Each of the two stationary magnetic coils may be configured to generate an axial magnetic field along the linear axis of movement of the permanent magnet. The permanent magnet itself is preferably arranged between the two axially spaced stationary magnetic coils. Thus, by alternatingly activating one of the two magnetic coils at a time, the slidably mounted permanent magnet may be actuated to move in a reciprocating linear movement between the two stationary magnetic coils. Likewise, the two stationary magnetic coils may be each powered by alternating currents that are phase-shifted, for example by 180°. Thus, the slidably mounted permanent magnet may be always attracted by either one of the two coils and repelled by the respective other one, which also causes a reciprocating linear movement of the permanent magnet and the capsule attached thereto.

As a consequence, in either of the above described configurations and operation modes, the capsule may be effectively shaken which advantageously causes an efficient de-agglomeration of the aerosol-forming powder within the capsule.

For supporting its linear movement, the at least one permanent magnet may be mounted on a linear shaft. The linear shaft itself may be slidably mounted within the device housing. Accordingly, the aerosol-generating device, in particular the magnetic actuator may comprise at least one, preferably two bearings, such as slide bearings, for supporting the linear shaft. The linear shaft may be also used for connecting the capsule to the actuator. In particular, the linear shaft may be attached to or may be part of a piercing tube that is configured to pierce the capsule, in particular to piercingly couple with the capsule. The piercing tube may be also configured to fluidly connect the interior of the capsule with the airflow passage through the device housing. Accordingly, the linear shaft may be also hollow. For example, the rotational shaft may be a tube that is fluidly connected to or part of the airflow passage through the device housing.

According to yet another configuration, the magnetic actuator of the present invention may be a reluctance actuator. Reluctance actuators typically comprise a stationary magnetic coil as well as a movable armature comprising a magnetic material, that is, a magnetizable material such as steel or iron. In operation, the magnetic coil causes the armature to move in a direction that increases the inductance of the coil. Thus, the magnetic coil acts as electric magnet which attracts the armature upon running an electrical current through the coil. The armature in turn may be used to provide a mechanical force to some mechanism. Advantageously, reluctance actuators may be directly controlled, for example by an electric circuitry, and thus have very quick reaction times. The force applied to the armature is proportional to the change in inductance of the coil with respect to the change in position of the armature, and the current flowing through the coil. The magnetic actuator may be a rotational reluctance actuator, such as a reluctance motor. Likewise, the magnetic actuator may be a linear reluctance actuator, such as solenoid actuator. In either case, the reluctance actuator comprises a rotationally or linearly movable armature, respectively, which may be connectable to the capsule.

According to a specific configuration, the magnetic actuator may comprise at least one stationary magnetic coil as well as a movable armature which comprises at least one resilient cantilever arm. The cantilever is connectable to a powder-containing capsule to be received with the device housing. Furthermore, the cantilever is configured to vibrate in response to a magnetic field of the stationary magnetic coil such as to cause a vibrational movement of the capsule when being connected to the armature.

The cantilever arm may have a fixed end attached to the device housing and a freely moveable end opposite to the fixed end. Advantageously, this one-sided mounting facilitates a vibrational movement of the cantilever arm.

At least a portion of the cantilever arm, such as the freely moveable end, may comprise a magnetic material, in particular a ferromagnetic or ferrimagnetic material, such as steel or iron. The magnetic material is configured to interact with magnetic field of a stationary magnetic coil such as to move in a direction that increases the inductance of the coil. Thus, by powering the stationary magnetic coil with a current at a pre-defined frequency, either in a pulsed mode or a continuous mode, the resilient cantilever is deflected when the coil is switched on, and reflected when the coil is switched off. As a consequence, the cantilever arm is vibrating in response to the magnetic field of the stationary magnetic coil. Thus, when being connected to a capsule, the cantilever arm transmits its vibrational movement onto the capsule, which advantageously leads to an efficient de-agglomeration of the aerosol-forming powder contained in the capsule.

Preferably, each cantilever arm comprises an additional mass at its freely moveable distal end for increasing the inertia of the cantilever arm. Advantageously, this enables the vibrating cantilever arms to have larger impact on the capsule.

Preferably, the magnetic actuator or the armature, respectively, comprises a plurality of said cantilever arms which are arranged such as to form an enclosing docking port for receiving the capsule. For example, the magnetic actuator or the armature, respectively, may comprise at least three cantilever arms which are circularly arranged at an inner wall of the device housing such as to form a basket-like enclosing docking port for receiving a capsule therein. In particular, the resilient cantilever arms may form a clamping docking port, wherein each cantilever arm exerts a spring-load onto a capsule when being received in the docking port. Thus, the armature advantageously provides a holder for securely holding a capsule within the device housing.

The aerosol-generating device may comprise at least one spring element coupled to the armature for exerting a reset force to the armature. Likewise, the aerosol-generating device may comprise at least one spring element connectable to the capsule for exerting a reset force to the capsule when being received within the device housing. Advantageously, the spring element facilitates a reciprocating movement of the armature and the capsule, respectively, which in turn intensifies the de-agglomeration of the aerosol-forming powder within the capsule. The spring element may be a spiral spring or torsional spring.

As described above, the aerosol-generating device according to the present invention comprises a device housing having an airflow passage therethrough into which the aerosol-forming powder is to be discharged to form an aerosol. Accordingly, the device housing may comprise at least one airflow inlet and at least one airflow outlet, wherein the airflow passage may extend between the airflow inlet and the airflow outlet. As used herein, the term 'airflow inlet' is used to describe one or more apertures through which air may be drawn into the aerosol-generating device. Similarly, the term 'airflow outlet' is used to describe one or more apertures through which air may be drawn out of the aerosol-generating device. The airflow outlet may be provided in a mouthpiece of the aerosol-generating device.

When being received within the device housing, the interior of the capsule is to be fluidly connected with the airflow passage such as to allow the aerosol-forming powder within the capsule to be discharged into the airflow passage. For this, the capsule may comprise at least one pre-formed discharge opening through which aerosol-forming powder may be escape from the interior of the capsule when being received within the device housing. For example, the capsule may comprise a powder-permeable casing, such as a mesh-like casing. When the capsule is received in the device housing, the airflow passage preferably passes along the exterior of the capsule, in particular along the outer surface of the capsule such that the aerosol-forming powder may be directly discharged into the airflow passage. In order to prevent aerosol-forming powder to unintentionally escape through the pre-formed discharge opening(s) prior to inserting the capsule into the aerosol-generating device, the capsule may comprise a protective covering. The protective covering may cover at least the discharge opening(s) or even the entire capsule. Prior to inserting the capsule into the aerosol-generating device, the protective covering is to be removed such as to free the at least one discharge opening.

Likewise, the aerosol-generating device may comprise at least one piercing element that is configured to pierce the capsule, in particular to piercingly couple with the capsule, that is a casing of the capsule, and to fluidly connect the interior of the capsule with the airflow passage. For this, the piercing element may comprise a hollow shaft portion in fluid communication with the airflow passage as well as at least one aperture in the hollow shaft portion that is arranged within the capsule when being pierced. Thus, the at least one aperture is in fluid communication with the interior of the capsule thereby allowing aerosol-forming powder to be discharged into the airflow passage. Preferably, the hollow shaft portion comprises a powder-permeable shaft portion, for example mesh-like or perforated shaft portion, such as to provide a plurality of apertures in fluid communication with the interior of the capsule. Preferably, the piercing element is a piercing tube. Accordingly, the piercing tube may comprise at least one a powder-permeable shaft portion, such as mesh-like or perforated shaft portion.

The piercing element or tube may either end up in the interior of the capsule or may pass through the entire capsule. Preferably, the airflow passage passes through the interior of the capsule. For this, the aerosol-generating device may comprise a piercing tube that passes through the entire capsule as described above. Alternatively, the aerosol-generating device may comprise at least two piercing tubes, in particular a pair of opposing piercing tubes, which end up in the interior of the capsule, wherein one of the piercing tube provides a feed-in and the other one provides a feed-out of the airflow passage. One of the piercing tubes, in particular a piercing tube that provides a feed-out, may be attached to a mouthpiece of the aerosol-generating device. In either case, the airflow passage leads through the piercing tube(s). Or vice versa, the piercing elements are part of the airflow passage or provide at least a portion of the airflow passage.

Preferably, the piercing element or the piercing tube is movably mounted in the device housing such as to allow a movement of a piercingly coupled capsule generated by the magnetic actuator.

The piercing element or tube may be attached to the magnetic actuator to couple the capsule to the magnetic actuator. Preferably, the piercing tube may be part of or may be a rotational shaft or a linear shaft of the magnetic actuator. Advantageously, this allows for designing a very compact device.

The aerosol-generating device may further comprise an electrical heater for warming or even heating the aerosol-forming powder in the capsule when being received in the device housing. Providing thermal energy to the powder advantageously supports the dispersion of the powder particles and thus intensifies the aerosol formation. In addition, warming or heating advantageously keeps the powder dry. The electrical heater may be a resistive heater or an inductive heater. Preferably, the electrical heater is an inductive heater because inductive heating allows for contactless heating of the powder in the capsule, which proves advantageous with regard to the movement to be induced onto the capsule. The inductive heater may comprises an induction source for generating an alternating electromagnetic field and a susceptor that heats up due to at least one of, eddy currents or hysteresis losses, that are induced by the alternating electromagnetic field in the susceptor material. For generating the alternating electromagnetic field, the induction source preferably comprise at least one inductor coil. Advantageously, a magnetic coil of the magnetic actuator may be also used as inductor coil for inductively heating the aerosol-forming powder. Likewise, another part of the magnetic actuator may be used as susceptor. Preferably, at least a portion of a movable armature of the magnetic actuator may be used as susceptor. As described above, the movable armature is configured to get connected to the capsule and may thus advantageously provide a direct thermal contact to the capsule. Likewise, by choosing suitable materials, the piercing tube or the capsule itself may be used as susceptor. Alternatively, the aerosol-forming powder may comprise a susceptor material.

The aerosol-generating device may further comprise an electric circuitry for operating and controlling the device, in particular for operating and controlling the magnetic actuator and—if present—the electrical heater. The electric circuitry may comprise a microprocessor, a microcontroller, or other electronic circuitry capable of providing control. In particular, the electric circuitry may be configured to control a supply of current to the magnetic actuator and—if present—to the electrical heater. The electric circuitry may be configured to operate the magnetic actuator and—if present—the electrical heater either continuously following an activation of the device by a user or intermittently, such as on a puff basis. Preferably, the electric circuitry includes least one of a DC or an AC generator, in particular a DC/AC inverter that is configured to supply current to the magnetic actuator, in particular to a magnetic coil or magnetic coil assembly of the magnetic actuator. The electric circuitry may further comprise least one of a DC or an AC generator that is configured to supply current to the electrical heater, if present. In particular, the electric circuitry may further comprise an AC generator that is configured to supply a high-frequency oscillating current to an inductor coil of an inductive heater, if present. As used herein, a high-frequency oscillating current means an oscillating current having a frequency between 500 kHz and 30 MHz, preferably between 1 MHz and 10 MHz and more preferably between 5 MHz and 7 MHz.

The aerosol-generating device may comprise a power supply for powering the electric circuitry, the magnetic actuator and—if present—the electrical heater. Preferably, the power supply is a battery such as a lithium iron phosphate battery. Alternatively, the power supply may be another form of charge storage device such as a capacitor. The power supply may require recharging and may have a capacity that allows for the storage of energy that is sufficient for one or more user experiences or for a predetermined number of puffs or discrete activations of the device.

The aerosol-generating device may comprise a main body and a mouthpiece which is removably attached to the main body. As used herein, the term 'mouthpiece' means a portion of the device that is placed into a user's mouth in order to directly inhale an aerosol generated by the aerosol-generating system. Accordingly, the mouthpiece may comprise an airflow outlet, in particular the airflow outlet of the airflow passage mentioned above, that is configured to convey an aerosol generated within the device housing to a user's mouth.

The aerosol-generating device, in particular the main body of the aerosol-generating device may comprise a cavity within the device housing for receiving a powder containing capsule.

The aerosol-generating device described herein may be a "passive" device that utilizes only the inhalation airflow created by a user to create airflow through the device housing of the aerosol-generating device.

The aerosol-generating device may include a puff sensor, such as a microphone, for detecting when a user puffs on the device, in particular on a mouthpiece. The puff sensor may be part of the electric circuitry which may be configured to activate the magnetic actuator and—if present—the electrical heater, when a puff is detected.

According to the invention there is also provided an aerosol-generating system comprising an aerosol-generating device according to the invention and as described herein as well as a capsule containing an aerosol-forming powder, wherein the capsule is configured to be used with the aerosol-generating device.

As mentioned above, the capsule itself may be directly actuated by a stationary part of the actuator, and thus, may constitute the movable part of the actuator. Yet, the capsule does not need to be or even is not part of the actuator or the aerosol-generating device. Preferably, the capsule is a stand-alone article. In this configuration, the stationary part of the actuator may just comprise a stationary magnetic coil for generating a magnetic field within the device housing. Accordingly, the capsule may be configured to move in response to a magnetic field of the stationary magnetic coil when being received in the device housing. For this, the capsule may comprise at least one of a magnetic coil, a magnetic material or a permanent magnet, each being configured to move in response to a magnetic field of the stationary magnetic coil of the aerosol-generating device such as to cause a movement of the capsule.

Of course, the magnetic actuator may also comprise—in addition to the stationary part—a movable part, such as a movable armature that is connectable to the capsule and configured to move in response to a magnetic field of the stationary part. In this configuration, the stationary part of the actuator may generate a magnetic force which directly impacts on both, the capsule as well as the movable part of the actuator.

Preferably, the capsule is a consumable, in particular a consumable to be discarded after a single use.

The capsule may be received in the device housing such as to be rotated around or linearly moved along a longitudinal axis of the capsule body.

The capsule may have any suitable size or shape. For example, the capsule may be cylindrical. Preferably, the capsule may be a sleeve having rounded end caps at both ends.

The capsule may comprise two capsule halves, for example made of injection molded polymers. Each half may include at least one pierceable portion. At least one half may be filled with aerosol-forming powder prior to assembling both halves together. The halves may have different diameters such that upon assembly one half encompasses a portion of the other half in a telescoping manner. Accordingly, the capsule may be a two-piece telescoping capsule.

The capsule may have a length of, for example, between about 4 mm and about 20 mm, preferably of about 16 mm. The capsule may have a diameter or a width of, for example, between about 4 mm and about 10 mm, preferably of about 6 mm. The capsule may have a thickness of, for example, between about 0.1 mm and about 1.0 mm, preferably between about 0.2 mm and about 0.4 mm.

The material and the thickness of the capsule wall are preferably such as to allow the piercing tube to readily pierce the capsule wall. Suitable materials of the capsule may be, for example, metal, gelatin, or plastics. In particular, suitable materials of the capsule may comprise stiffened cigarette or filter paper, hydroxypropyl methylcellulose (HPMC), polyvinyl alcohol (PVA), pullulan. Likewise, the material of the capsule may be starch based.

The aerosol-forming powder may comprise a nicotine powder. The term "nicotine" refers to nicotine and nicotine derivatives such as nicotine salts. Accordingly, the nicotine powder may be a nicotine salt or nicotine salt hydrate. Suitable nicotine salts or nicotine salt hydrates include, for example, nicotine tartrate, nicotine aspartate, nicotine lactate, nicotine glutamate, nicotine bitartrate, nicotine salicylate, nicotine fumarate, nicotine mono-pyruvate, nicotine hydrochloride, and combinations thereof.

The nicotine powder may have any suitable particle size distribution for pulmonary delivery of the nicotine to a user. In particular, at least about 90 weight percent (wt %) of the nicotine powder may have a particle size of about 10 micrometers or less, preferably about 7 micrometers or less.

The nicotine powder preferably has a mean average diameter ranging from about 0.1 to about 10 micrometers, more preferably from about 1 to about 7 micrometers, particularly preferably from about 2 to 6 about micrometers.

The nicotine powder particles may be surface modified, for example the nicotine salt particles may be coated. A preferred coating material is L-leucine. Particularly suitable nicotine powder particles include L-leucine coated nicotine bitartrate, L-leucine coated nicotine glutamate and L-leucine coated asparate.

The capsule preferably contains between about 5 and about 20 milligrams of nicotine powder, in particular about 10 milligrams of nicotine powder. Preferably, the capsule preferably contains sufficient nicotine powder to deliver between about 10 and about 30 puffs to a user.

The nicotine powder described herein preferably is carrier-free. Being carrier-free allows the nicotine powder to be inhaled and delivered to the user's lungs at inhalation or airflow rates that are similar to typical smoking regime inhalation or airflow rates. In addition, since the nicotine powder is carrier-free, the airflow path of the inhaler can have simple geometry or a simple configuration.

Nevertheless, the aerosol-forming powder may further contain carrier particles that serve to increase the fluidization of the active particles and to improve the dose uniformity by acting as a diluent or bulking agent in a formulation.

Alternatively or in addition to nicotine powder, the aerosol-forming powder may also comprise another active agent or ingredient, such as an active pharmaceutical material. This active agent or ingredient can be blended in the same capsule. The second active agent or ingredient can have a similar mean average diameter size range as the nicotine powder described above.

Further features and advantages of aerosol-generating system and the capsule according to the invention have been described above with regard to aerosol-generating device according to the invention and will not be repeated.

The invention will be further described, by way of example only, with reference to the accompanying drawings, in which.

Figure 1:
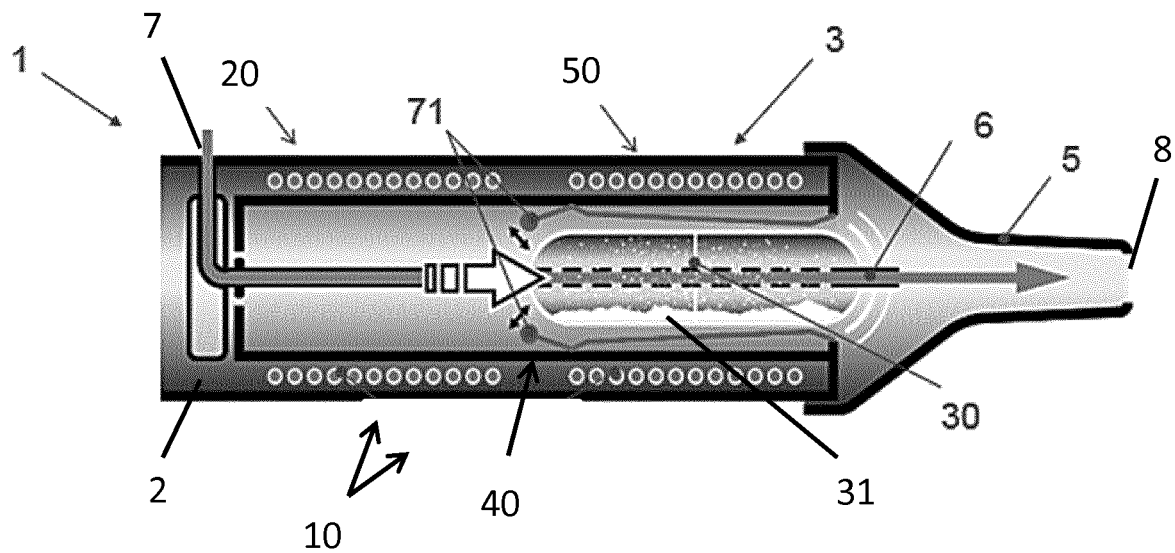
FIG. 1 shows a cross-sectional view of an aerosol-generating system according to first embodiment of the invention.

FIG. 1 schematically illustrates an aerosol-generating system according to a first embodiment of the present invention that is based on dispersing an aerosol-forming powder into an airflow. According to the invention, the aerosol-generating system includes two components, an aerosol-generating device 1 and a capsule 30 for use with the device, which contains an aerosol-forming powder 31 to be dispersed into an airflow through the device.

With reference to FIG. 1, the aerosol-generating device 1 comprises a main body 2 and mouthpiece 5 which is removably attached to the main body 2. The mouthpiece 5 may be connected to the main body 2 by any kind of connection, such as by a hinged connection, a snap fitting, or a screw fitting. The housing of the main body 2 and the mouthpiece 5 together form a housing 3 of the device. According to the invention, the device housing 3 is configured to receive a powder containing capsule 30 therein. In the present embodiment, the capsule 30 is mainly received within a cavity formed in the main body 2. For receiving the capsule 30 therein, the mouthpiece 5 may be removed from the main body 2 to allow the capsule to be inserted. Upon insertion of the capsule 30, the mouthpiece 5 is again attached to the main body 2 such that the capsule is completely enclosed by the device housing 3.

The aerosol-generating device 1 further comprises an airflow passage through the device housing 3 (indicated by the dashed arrow in FIG. 1) into which the aerosol-forming powder 31 is to be discharged. In the present embodiment, the airflow passage extends from a lateral airflow inlet 7 in the main body 2 through the capsule receiving cavity towards an airflow outlet 8 at the end tip of the mouthpiece 5. In use, a user may puff on the mouthpiece 5 to draw air through the airflow inlet 7 into the device housing 3 and further through the airflow outlet 8 into the user's mouth. In that sense, the aerosol-generating device 1 according to FIG. 1 is a "passive" device that utilizes only the inhalation airflow created by a user to generate an airflow through the device housing 3.

In order to allow the aerosol-forming powder 31 in the capsule 30 to be dispersed into the airflow through the device housing 3, the aerosol-generating device 1 further comprises a piercing tube 6 which is part of the airflow passage, or vice versa, through which the airflow passage extends through. The piercing tube 6 is configured to pierce the capsule 30, in particular to piercingly couple with the capsule 30, and to fluidly connect the interior of the capsule 30 with the airflow passage. In the present embodiment, the piercing tube 6 is a cannula-like metal tube that is sufficiently stiff to pierce the capsule 30 all the way through. The piercing tube 6 may be attached to the mouthpiece 5. Thus, upon insertion of the capsule 30 into the device housing 3, the capsule 30 is automatically pierced by re-assembling the mouthpiece 5 and the main body 2. Alternatively, the piercing tube 6 may be separate from the main body 2 and the mouthpiece 5, and only in contact with the capsule 30 upon piercing the same. The piecing tube 6 is open at both ends allowing air to flow therethrough, that is, from the airflow inlet 7 through the tube 6 towards the airflow outlet 8 in the mouthpiece 5. The piercing tube 6 further comprises a perforated powder-permeable tube section, such as a mesh-like wall section. Upon piercing the capsule 30, the perforated powder-permeable tube section is located inside the capsule 30 such as to provide a fluid communication between the airflow passing through the tube 6 and the aerosol-forming powder 31 within the capsule 30. Thus, when a user puffs on the mouthpiece 5 to draw air along the airflow passage, aerosol-forming powder 31 is readily entrained by and dispersed into the airflow through the piercing tube 6.

Figure 2:
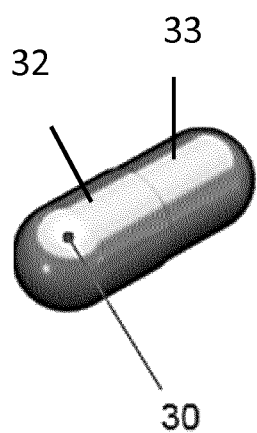
FIG. 2 shows a perspective view of a capsule containing an aerosol-forming powder as used in the aerosol-generating system according to FIG. 1.

FIG. 2 shows an exemplary embodiment of a powder containing capsule used in combination with the aerosol-generating device 1 according to FIG. 1. The capsule 30 basically is of cylindrical shape. In particular, the capsule 30 may comprise two capsule halves 32, 33, wherein each half is a cylindrical sleeve having a hemispheric end cap or bottom. At least one half may be filled with aerosol-forming powder 31 prior to assembling both halves together. The halves 32, 33 may have different diameters such that upon assembly one half encompasses a portion of the other half in a telescoping manner. Accordingly, the capsule 30 may be a two-piece telescoping capsule. The capsule 30 may be made of metal, gelatin, or plastics. For example, the capsule 30 may comprise two capsule halves made of injection molded polymers. Each half may include at least one pierceable portion. The thickness of the capsule wall preferably is between 0.2 mm and 0.4 mm such as to allow the piercing tube 6 to readily pierce the capsule wall. In the present embodiment, the capsule 30 contains about 10 milligrams of nicotine powder which is sufficient to deliver between about 15 puffs to a user. Preferably, the capsule 30 is a powder containing consumable to be discarded after a single use. Of course, it may be also possible that the capsule is configured to be refilled such as to allow for multiple use of the capsule.

According to the present invention, the aerosol-generating device 1 further comprises a magnetic actuator 10 that is configured to generate a movement of the capsule 30 when being received in the device housing 3 for de-agglomerating the aerosol-forming powder 31 in the capsule 30. Preferably, the magnetic actuator 10 comprise a stationary magnetic coil 20 for generating a magnetic field as well as a movable armature 40 that is connectable to the capsule 30 and configured to move in response to the magnetic field of the coil 20 such as to induce a powder de-agglomerating movement onto the capsule 30.

Figure 3:
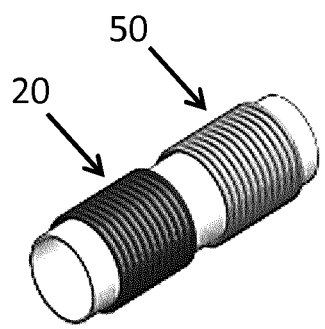
FIG. 3 shows a perspective view of a magnetic coil arrangement as used in the aerosol-generating system according to FIG. 1.

As regards the embodiment according to FIG. 1, the stationary magnetic coil 20 is a helical coil arranged within the main body 2. FIG. 3 shows further details of the actuator coil 20 that is wound onto a sleeve which may form a portion of the receiving cavity within the device housing 3. As can be seen from FIG. 1, the helical actuator coil 20 is arranged close to the inner surface of the device housing 3 forming the cavity for receiving the capsule 30.

The armature 40 is also arranged within the cavity of the main body 2, but axially offset to the helical coil 20. In the embodiment according to FIG. 1, the armature comprises four resilient cantilever arms 71 (only two of which are shown in FIG. 1) which are arranged such as to form an basket-like enclosing docking port for receiving the capsule 30 therein. Thus, when inserted into the device housing 3, the capsule 30 is not only in contacted with the cantilever arms 71, but also securely held due to the resilient cantilever arms 71 exerting a spring-load onto a capsule 30. The cantilever arms have a fixed end attached to the device housing 3 and a freely moveable distal end opposite to the fixed end such as to allow each arm to be deflected and thus to vibrate. At least a portion of each cantilever arm 71, preferably at least the freely moveable end, comprises a magnetic material, in particular a ferromagnetic or ferrimagnetic material, such as steel or iron. Due to this, each cantilever arm 71 may interact with the magnetic field of the coil 20 such as to move in a direction that increases the inductance of the coil 20. By powering the coil 20 with a current at a pre-defined frequency, either in a pulsed mode or a continuous mode, each cantilever 71 is deflected when the coil 20 is switched on, and reflected when the coil 20 is switched off. As a consequence, the cantilever arms are vibrating in response to the magnetic field of the coil 20, which advantageously leads to an efficient de-agglomeration of the aerosol-forming powder 31 in the capsule 30. Moreover, the vibrational movement of the cantilever arms 71 causes the powder 31 to be swirled up which facilitates the discharge of the powder 31 into the airflow passage and, thus, intensifies the aerosol formation during a user's puff. Preferably, each cantilever 71 arm comprises an additional mass at its freely moveable distal end for increasing the inertia of the cantilever arm. Advantageously, this enables the vibrating cantilever arms to have larger impact on the capsule.

In addition to the magnetic coil 20, the aerosol-generating device 1 according to FIG. 1 comprises a further magnetic coil 50 for generating an alternating electromagnetic field that is used to inductively warm or heat the aerosol-forming powder 31 within the capsule 30. As can be seen from FIG. 1 and FIG. 2, the inductor coil 50 is a helical coil similar to the actuator coil 20 that is arranged within the device housing 3 such as to surround the cantilever arms 71, the piercing tube 6 and the capsule 30. Due to the magnetic properties of the armature, each cantilever arm 71 constitutes a susceptor for interaction with the inductor coil 50. By applying an alternating current to the inductor coil 50, each cantilever arm 71 heats up due to eddy currents and/or hysteresis losses induced therein by the alternating electromagnetic field of the inductor coil 50. As the cantilever arms 71 are in close proximity to or even in contact with the capsule 30, the aerosol-forming powder 31 within in the capsule 30 may be readily warmed or heated. Likewise, by choosing suitable materials, the piercing tube 6 may also be used as susceptor for inductively warming or heating the powder 31 within the capsule 30. Advantageously, providing the powder 31 with thermal energy facilitates the dispersion of the powder particles in the airflow and thus intensifies the aerosol formation. In addition, warming or heating advantageously keeps the powder 31 dry.

Both, the actuator coil 20 and the inductor coil 50, may be operated and controlled by an electric circuitry of the aerosol-generating device 1 (not shown). Preferably, the aerosol-generating device 1 may also comprise an airflow sensor (not shown) such as to activate the actuator coil 20 and the inductor coil 50 in response to a user puff, detected by the sensor.

Figure 4:
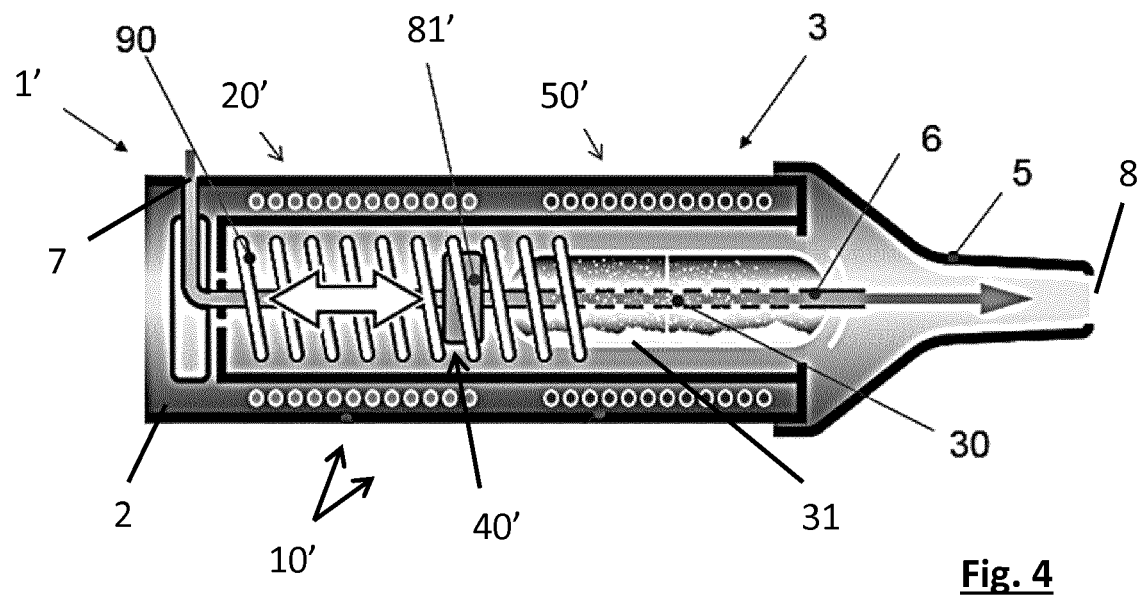
FIG. 4 shows a cross-sectional view of an aerosol-generating system according to second embodiment of the invention.

FIG. 4 schematically illustrates a second embodiment of the aerosol-generating system, which also comprises an aerosol-generating device 1' and a powder containing capsule 30 for use with the device 1'. The capsule 30 is identical to the capsule 30 shown in FIG. 2 and as used in combination with the device 1 according to FIG. 1. In general, the aerosol-generating device 1' according to FIG. 4 also is very similar to the aerosol-generating device 1 according to FIG. 1. Therefore, corresponding features are denoted with the same reference numbers. As far as in accordance with the first embodiment, reference is made to the description of FIGS. 1 to 3. The aerosol-generating devices 1, 1' according to the first and second embodiment essentially only differ in the magnetic actuators 10, 10' used to generate a movement of the powder de-agglomerating of the capsule 30. In contrast to the first embodiment, the magnetic actuator 10' of the second embodiment comprises a moving magnet actuator 10' that is configured to generate a reciprocating linear movement of the capsule 30. As can be seen from FIG. 4, the actuator 10' comprises a helical stationary magnetic coil 20' and a linearly movable armature 40'. The linearly movable armature 40' comprises a slidably mounted permanent magnet 81' that is configured to linearly move in response to a magnetic field of the actuator coil 20' that surrounds the magnet 81'.

The permanent magnet 81' is mounted on a linear shaft which in turn is slidably mounted within the device housing 3. In the present embodiment, the linear shaft is part of the piercing tube 6 that is configured to pierce the capsule 30, in particular to piercingly couple with the capsule 30, and to fluidly connect the interior of the capsule 30 with the airflow passage extending therethrough.

Preferably, the permanent magnet 81' is a rare-earth magnet, such as a samarium-cobalt magnet or a neodymium magnet.

Figure 5:
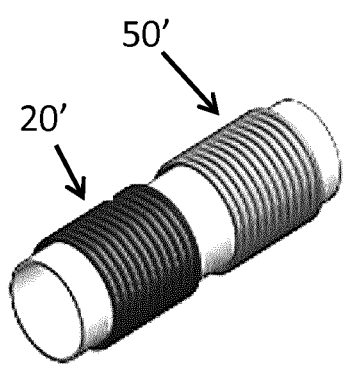
FIG. 5 shows a perspective view of a magnetic coil arrangement as used in the aerosol-generating system according to FIG. 4.

As shown in FIG. 5, the helical actuator coil 20' is essentially identical to the actuator coil 20' of the first embodiment as shown in FIG. 3. In operation, the actuator coil 20' generates an axial magnetic field along the linear axis of movement of the slidably mounted permanent magnet 81' (indicated by the double arrow in FIG. 4). The direction of magnetization of the magnet 81' is parallel to the axial field of the helical actuator coil 20' and parallel to the linear axis of movement. Depending on the orientation of the current used to power the actuator coil 20', the permanent magnet 81' is either repelled or attracted by the magnetic field of the coil 20'. Thus, applying an alternating current to the actuator coil 20' may cause a reciprocating linear movement of the permanent magnet 81' and of the capsule 30 connected thereto.

Alternatively, the actuator 10' may comprise a further stationary helical actuator coil 50' in addition to the actuator coil 20'. This further helical coil 50' is also arranged along the linear axis of movement of the permanent magnet 81' within the device housing 3. The permanent magnet 81' is preferably arranged between the two axially spaced actuator coils 20', 50'. Thus, by alternatingly activating one of the two magnetic coils 20', 50' at a time, the slidably mounted permanent magnet 81' is actuated to move in a reciprocating linear movement along the axial direction of the piercing tube 6. Likewise, the actuator coils 20'; 50' may be each powered by alternating currents that are phase-shifted, for example by 180°. Thus, the slidably mounted permanent magnet 81' is always attracted by either one of the two coils and repelled by the respective other one, which also causes a reciprocating linear movement of the permanent magnet 81' and the capsule 30 connected thereto.

The aerosol-generating device 1' further comprise a spiral spring 90 coupled to at least one of the armature 40' and the capsule 30 for exerting a reset force thereto that facilitates the reciprocating movement. The reset force of the spring 90 may also allow for operating the actuator 10' using one coil only that is powered by a DC current in a pulsed on-off mode. When switched on, the magnetic field of the coil may drive the magnet permanent 81 in a direction opposite to the reset force of the helical spring 90. Vice versa, when switched off, the reset force of the loaded spring 90 may drive the permanent magnet 81' back into the other direction. Thus, operating the coil in a pulsed on-off mode causes the permanent magnet 81 to linearly oscillate.

In either of the above described configurations and operation modes, the reciprocating linear movement of the permanent magnet 81' causes an efficient de-agglomeration and swirl-up of the aerosol-forming powder 31 within the capsule 30.

Alternatively or in addition, the further stationary coil 50' may be used to inductively warm or heat the aerosol-forming powder 31 within the capsule 30 as described above with respect the first embodiment shown in FIG. 1. As regards the second embodiment shown in FIG. 4, it is the piercing tube 6 which preferably is used as susceptor.

Figure 6:
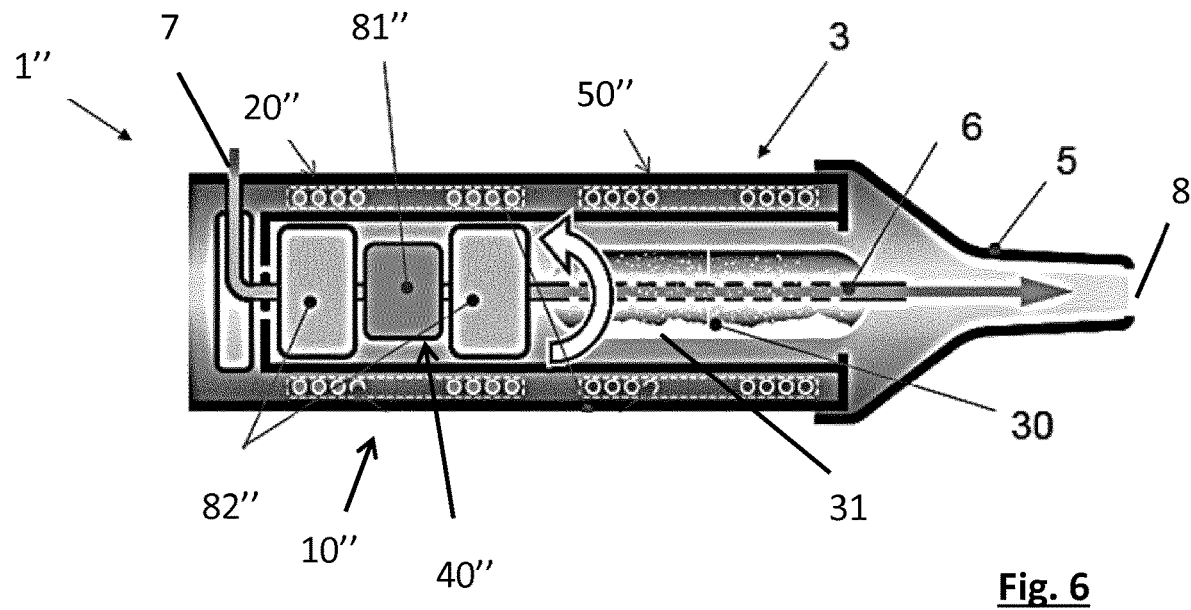
FIG. 6 shows a cross-sectional view of an aerosol-generating system according to third embodiment of the invention.

FIG. 6 schematically illustrates an aerosol-generating system in accordance with a third embodiment of the invention. The system also comprises an aerosol-generating device 1" as well as a powder containing capsule 30 for use with the device 1" which is identical to the capsule 30 shown in FIG. 2 and as used in combination with the devices 1, 1' shown in FIGS. 1 and 4. In general, the aerosol-generating device 1" of the third embodiment also is very similar to the devices 1, 1' according to the first and second embodiment. Therefore, corresponding features are denoted with the same reference numbers. As far as in accordance with the first and second embodiment, reference is made to the description of FIGS. 1 to 5.

In contrast to the devices 1, 1' shown in FIGS. 1 and 4, the aerosol-generating device 1" according to the FIG. 6 comprises a rotary magnet actuator 10" that is configured to generate a rotary movement of the capsule 30. For this, the magnetic actuator 10" comprises a stationary magnetic coil 20" and a rotatable armature 40". The rotatable armature 40" comprises a rotatably mounted permanent magnet 81" surrounded by the coil 20 "that is configured to rotate in response to a magnetic field of the coil such as to cause a rotational movement of the capsule 30 connected thereto. The permanent magnet 81" is mounted on a rotational shaft which in turn is rotationally supported by two bearings 82" within the device housing 3. In particular, the rotational shaft is part of the piercing tube 6 that is configured to pierce the capsule, in particular to piercingly couple with the capsule 30, and to fluidly connect the interior of the capsule 30 with the airflow passage extending therethrough.

In the present embodiment, the permanent magnet 81' is a rare-earth magnet, such as a samarium-cobalt magnet or a neodymium magnet, which generates a radial permanent magnetic field.

Figure 7:
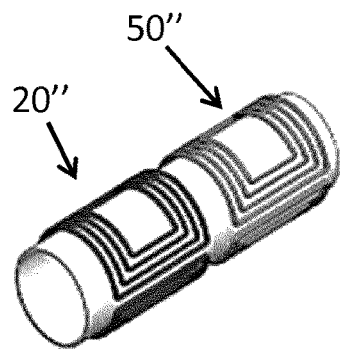
FIG. 7 shows a perspective view of a magnetic coil arrangement as used in the aerosol-generating system according to FIG. 6.

As shown in FIG. 7, the actuator coil 20" is a radially segmented coil configured to generate an alternating magnetic field directed perpendicularly to the surface of the device housing 3. In particular, the segmented coil configuration allows for generating a rotating magnetic field.

The alternating magnetic field generated by the actuator coil 20" interacts with the radial magnetic field of the permanent magnet 81 such as to cause the latter to rotate. Such rotation, allowed by bearings 82, is transferred to the piercing tube 6 which lastly causes a rotation of the capsule 30 and the powder 31 contained therein. In order to intensify the de-agglomeration of the powder 31 within the capsule 30, the actuator coil 20" may be operated in a pulsed mode such as to generate a magnetic field that is alternatingly switched on and off and thus causes a pulsed rotational movement of the armature and the capsule connected thereto. Alternatively, the actuator coil 20" may be operated such as to generate a slow continuous rotation movement of the armature and the capsule connected thereto. The slow continuous rotation movement may comprise a rotational speed equal to or less than 200 rounds per minute, in particular equal to or less than 100 rounds per minute, preferably equal to or less than 60 rounds per minute.

As can be further seen from FIG. 7, the aerosol-generating device 1" according to the third embodiment may also comprise a further coil 50" which may be used, similarly to the first and second embodiment, to inductively warm or heat the powder. The inductor coil 50" may be similar to the actuator coil 20".

The invention claimed is:

1. An aerosol-generating device for generating an aerosol by dispersing an aerosol-forming powder into an airflow, the device comprising:
a device housing comprising an airflow passage therethrough and being configured to receive a capsule containing the aerosol-forming powder to be discharged into the airflow passage,
a magnetic actuator being configured to generate a movement of the capsule when being received in the device housing for de-agglomerating the aerosol-forming powder within the capsule, wherein the magnetic actuator comprises at least one stationary magnetic coil within the device housing for generating a magnetic field, wherein the magnetic actuator further comprises a movable armature configured to move in response to the magnetic field of the stationary magnetic coil, the movable armature being connectable to the capsule for transferring a movement of the armature onto the capsule, wherein the movable armature comprises or forms a holder to receive and hold the capsule within the device housing;
further comprising at least one piercing tube configured to pierce the capsule and to fluidly connect the interior of the capsule with the airflow passage;
wherein the piercing tube is attached to the magnetic actuator to couple the capsule to the magnetic actuator.

2. The aerosol-generating device according to claim 1, wherein the stationary magnetic coil is a flat spiral magnetic coil or a helical magnetic coil.

3. The aerosol-generating device according to claim 1, wherein the movable armature comprises at least one rotatably mounted permanent magnet configured to rotate in response to the magnetic field of the stationary magnetic coil such as to cause a rotational movement of the capsule when being connected to the armature.

4. The aerosol-generating device according to claim 1, wherein the movable armature comprises at least one slidably mounted permanent magnet configured to linearly move in response to the magnetic field of the stationary magnetic coil such as to cause a linear movement of the capsule when being connected to the armature.

5. The aerosol-generating device according to claim 1, wherein the movable armature comprises at least one resilient cantilever arm at least a portion of which comprises a magnetic material, wherein the cantilever arm is configured to vibrate in response to the magnetic field of the stationary magnetic coil such as to cause a vibrational movement of the capsule when being connected to the armature.

6. The aerosol-generating device according to claim 5, wherein the movable armature comprises a plurality of said cantilever arms being arranged to form an enclosing docking port for receiving the capsule.

7. The aerosol-generating device according to claim 1, further comprising at least one spring element coupled to the armature for exerting a reset force thereto.

8. The aerosol-generating device according to claim 1, wherein the piercing tube comprises at least one a powder-permeable shaft portion.

9. The aerosol-generating device according to claim 1, further comprising an electrical heater for heating the aerosol-forming powder in the capsule when being received in the device housing.

10. An aerosol-generating system comprising an aerosol-generating device according to claim 1 and a capsule configured to be used with the aerosol-generating device, wherein the capsule contains an aerosol-forming powder.

11. The aerosol-generating system according to claim 10, wherein the capsule comprises at least one of a magnetic coil, a magnetic material or a permanent magnet, each configured to move in response to the magnetic field of the stationary magnetic coil of the aerosol-generating device when the capsule is received in the device housing of the aerosol-generating device such as to cause a movement of the capsule.

12. An aerosol-generating device for generating an aerosol by dispersing an aerosol-forming powder into an airflow, the device comprising:
- a device housing comprising an airflow passage therethrough and being configured to receive a capsule containing the aerosol-forming powder to be discharged into the airflow passage,
- a magnetic actuator being configured to generate a movement of the capsule when being received in the device housing for de-agglomerating the aerosol-forming powder within the capsule, wherein the magnetic actuator comprises at least one stationary magnetic coil within the device housing for generating a magnetic field, wherein the magnetic actuator further comprises a movable armature configured to move in response to the magnetic field of the stationary magnetic coil, the movable armature being connectable to the capsule for transferring a movement of the armature onto the capsule, wherein the movable armature comprises or forms a holder to receive and hold the capsule within the device housing;
- wherein the movable armature comprises at least one slidably mounted permanent magnet configured to linearly move in response to the magnetic field of the stationary magnetic coil such as to cause a linear movement of the capsule when being connected to the armature.

13. An aerosol-generating device for generating an aerosol by dispersing an aerosol-forming powder into an airflow, the device comprising:
- a device housing comprising an airflow passage therethrough and being configured to receive a capsule containing the aerosol-forming powder to be discharged into the airflow passage,
- a magnetic actuator being configured to generate a movement of the capsule when being received in the device housing for de-agglomerating the aerosol-forming powder within the capsule, wherein the magnetic actuator comprises at least one stationary magnetic coil within the device housing for generating a magnetic field, wherein the magnetic actuator further comprises a movable armature configured to move in response to the magnetic field of the stationary magnetic coil, the movable armature being connectable to the capsule for transferring a movement of the armature onto the capsule, wherein the movable armature comprises or forms a holder to receive and hold the capsule within the device housing;
- further comprising at least one spring element coupled to the armature for exerting a reset force thereto.

* * * * *